United States Patent
De Fraine

[11] Patent Number: 5,723,471
[45] Date of Patent: Mar. 3, 1998

[54] PYRIMIDINE FUNGICIDES

[75] Inventor: Paul John De Fraine, Wokingham, United Kingdom

[73] Assignee: Zeneca Limited, London, England

[21] Appl. No.: 687,545

[22] PCT Filed: Feb. 27, 1996

[86] PCT No.: PCT/GB95/00399

§ 371 Date: Aug. 7, 1996

§ 102(e) Date: Aug. 7, 1996

[87] PCT Pub. No.: WO95/24396

PCT Pub. Date: Sep. 14, 1995

[30] Foreign Application Priority Data

Mar. 7, 1994 [GB] United Kingdom ............ 9404375

[51] Int. Cl.⁶ .................... C07D 239/46; A01N 43/54
[52] U.S. Cl. .................... 514/274; 544/312; 544/314
[58] Field of Search ................ 514/274; 544/312, 544/314

[56] References Cited

FOREIGN PATENT DOCUMENTS

| | | |
|---|---|---|
| 0 242 070 | 10/1987 | European Pat. Off. |
| 0 242 081 | 10/1987 | European Pat. Off. |
| 0 382 375 | 8/1990 | European Pat. Off. |
| 0 391 451 | 10/1990 | European Pat. Off. |
| 0 393 861 | 10/1990 | European Pat. Off. |
| 0 398 692 | 11/1990 | European Pat. Off. |
| 0 405 782 | 2/1991 | European Pat. Off. |
| 0 430 471 | 6/1991 | European Pat. Off. |
| 0 468 684 | 1/1992 | European Pat. Off. |
| 0 468 695 | 1/1992 | European Pat. Off. |

*Primary Examiner*—John M. Ford
*Attorney, Agent, or Firm*—Joseph R. Snyder

[57] ABSTRACT

A fungicidal compound of formula (I) or a stereoisomer thereof, wherein R is H or $CH_3$, A is CH or N, and B is $OCH_3$ or $NHCH_3$.

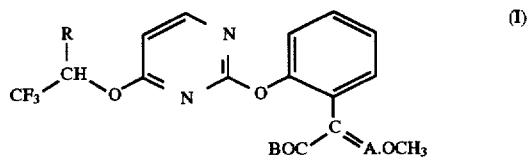

9 Claims, No Drawings

PYRIMIDINE FUNGICIDES

This application is a 35 U.S.C.§371 national stage filing of PCT/GB95/00999 filed 27 Feb., 1996.

The present invention relates to novel pyrimidine derivatives, to processes for preparing them, to compositions containing them and to methods of using them to combat fungi, especially fungal infections of plants.

Certain methyl 2-[2-(substituted pyrimidinyloxy)phenyl]3-methoxyacrylates are described in EP-A-0242081 together with their use as fungicides. Specifically mentioned are the compounds, methyl 2-[2-(4-trifluoromethylpyrimidin-2-yloxy)phenyl]-3-methoxyacrylate and methyl 2-[2-(4-methoxypyrimidin-2-yloxy)phenyl]-3-methoxyacrylate. It has now been found that the corresponding compounds containing a 4-(2,2,2-trifluoroethoxy) or 4-(1,1,1-trifluoroprop-2-oxy) substituent show unexpected advantages as plant fungicides in respect of vapour activity, foliar eradicant activity, spectrum of activity and/or systemicity.

Thus according to the present invention there is provided a compound of the general formula (I) (see later page of chemical formulae) or a stereoisomer thereof, wherein R is H or $CH_3$, A is CH or N, and D is $OCH_3$ or $NHCH_3$.

Because the carbon—carbon or carbon-nitrogen double bond of the group $DOC.C=A.OCH_3$ is unsymmetrically substituted, the compounds of the invention may be obtained in the form of mixtures of the (E)- and (Z)-geometric isomers. However, these mixtures can be separated into individual isomers by well known techniques, and this invention embraces such isomers and mixtures thereof in all proportions. The (E)-isomers are the more fugicidally active and therefore form a preferred embodiment of the invention.

In particular, the group W is $CH_3O.N=C.CO_2CH_3$, $CH_3O.N=C.CONHCH_3$ and more particularly $CH_3O.CH=C.CO_2CH_3$.

In one aspect the invention provides the (E)-isomer of the compound of formula (I.1). In another aspect the invention provides the (E)-isomer of the compound of formula (I.4). In other aspects the invention provides the (E)-isomers of the compounds of formulae (I.2), (I.3), (I.5) and (I.6).

The compounds of the invention of formula (I) [equivalent to formula (IA) when W is the group $DOC.C=A.OCH_3$] can be prepared by the steps illustrated in Scheme I. Throughout Scheme I, $R^1$ is an alkyl or aryl group, $R^2$ is $CF_3CH_2$ or $CF_3CH(CH_3)$, X is a halogen atom (eg Cl, Br, I), M is an alkali metal (eg sodium or potassium), T is hydrogen or an alkali metal (eg sodium or potassium), Ba is a base (eg sodium hydride or potassium carbonate), Ox is an oxidising agent (eg potassium permanganate or metachloroperbenzoic acid) and W is the group $DOC.C=A.OCH_3$ defined above or a group that can be transformed into $DOC.C=A.OCH_3$ using methods such as those already described in the literature.

The compounds of the invention can be prepared by reaction of the phenol of formula (II) with a pyrimidinyl sulphone of general formula (III), in the presence of a suitable base Ba. Alternatively, they can be prepared by reaction of a phenolate salt of formula (II) with the sulphone (III). Phenols of the formula (II), where W is $DOC.C=A.OCH_3$, can be prepared by methods described in, for example, EP-A-0242081, EP-A-0398692 and GB-A-2249092. The compounds of formula (III) can be prepared from the thiopyrimidine of general formula (IV) by oxidation with a suitable oxidising agent Ox in a suitable solvent such as aqueous acetic acid. The thiopyrimidine of formula (IV) can be prepared from the thiopyrimidine (V) by reaction with an alkoxide of formula $R^2OM$ in a suitable solvent such as N,N-dimethylformamide (DMF) or tetrahydrofuran (THF). The compound (V) where X is chlorine is available commercially.

Alternatively the compound of formula (I) can be prepared from the pyrimidine of general formula (VI), by reaction with an alkoxide of formula $R^2OM$, in a suitable solvent such as DMF. Compounds of general formula (VI) can be prepared by treating the phenol of formula (II) with a sulphone of general formula (VII) using a base Ba in a suitable solvent such as DMF. The sulphone of formula (VII) can be prepared from the pyrimidine of formula (V) by oxidation with a suitable oxidising agent Ox in a suitable solvent such as aqueous acetic acid or dichloromethane.

Alternatively, the invention compounds of formula (I) may be prepared from a compound of the formula (IA) where W is a group which can be converted by standard procedures described in the literature into the group $DOC.C=A.OCH_3$. For example, where W is the group $CH_3CO_2C.C=CH.OH$, $CH_3CO_2C.C=N.OH$ or $CH_3NHOC.C=N.OH$ it may be converted to the appropriate group $DOC.C=A.OCH_3$ by methylation with a compound $CH_3L$, wherein L is a leaving group such as halo or $CH_3SO_2.O$, in the presence of a convenient base Ba. Where W is the phenylglyoxylic acid derivative, $CO.CO_2CH_3$ or $CO.CONHCH_3$, it may be converted to the appropriate group $DOC.C=A.OCH_3$ by treatment with the Wittig reagent $Ph_3P=CH.OCH_3$, wherein Ph is phenyl, or with methylhydroxylamine.

The compounds (IA), where W is a group which can be transformed into the group $DOC.C=A.OCH_3$, can be prepared by reacting a phenol of formula (II) with a sulphone of formula (III) or by reacting a pyrimidine of formula (VI), derived from the phenol (II), with an alkoxide $R^2OM$ as described above. The phenol (II) can conveniently be prepared from an appropriately substituted phenylacetic acid derivative by methods known in the literature (see, for example, EP-A-0178826, EP-A-0254426, EP-A-0278595, EP-A-0299694 and EP-A-0398692).

The compounds of formula (I), wherein A is CH or N and B is $NHCH_3$, can also be prepared from the corresponding compounds wherein A is CH or N and B is OH, by methods set out in the literature and in other ways described in EP-A-0398692.

Compounds of the formula (IA.1), i.e. compounds (IA) where W is $CH_3CO_2.C=N.OCH_3$, and compounds of the formula (IA.2), i.e. compounds (IA) where W is $CH_3NH(O)C=N.OCH_3$, may also be prepared by the steps illustrated in Scheme 2.

Compounds of the formula (IA.1) may be prepared from the 2,3-benzofurandione-3-O-methyloxime (IX) by treating compound (IX) with the methoxide of formula $CH_3OM$ followed by treatment with the pyrimidinyl sulphone of general formula (III). The 2,3-benzofurandione-3-O-methyloxime of formula (IX) may be prepared by methylation of the 2,3-benzofurandione-oxime (VIII) with a compound $CH_3L$, wherein L is a leaving group such as halo or $CH_3SO_2.O$, in the presence of a convenient base Ba. The 2,3-benzofurandione-3-O-methyloxime (IX) and the 2,3-benzofurandione-oxime (VIII) may be prepared by methods described in WO 93/07116 (EP-A-0606251).

Compounds of the formula (IA.2) may be prepared by reaction of the phenol of formula (X) with a pyrimidinyl sulphone of general formula (III), in the presence of a suitable base Ba. The phenol of formula (X) may be prepared by treating the 2,3-benzofurandione-3-O-methyloxime of formula (IX) with methylamine. Alternatively the compound of formula (IA.2) may be obtained by treating the compound of general formula (IA.1) with methylamine.

The compounds of formula (I) are active fungicides and may be used to control one or more of the following pathogens: *Pyricularia oryzae* on rice and wheat and other *Pyricularia spp.* on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; *Cochliobolus spp., Helminthosporium spp., Drechslera spp. (Pyrenophora spp.), Rhynchosporium spp., Septoria spp.* (including *Mycosphaerella graminicola* and *Leptosphaeria nodorum*). *Pseudocercosporella herpotrichoides* and *Gaeumannomyces graminis* on cereals (e.g. wheat, barley, rye), turf and other hosts; *Cercospora arachidicola* and *Cercosporidium personatum* on peanuts and other Cercospora species on other hosts, for example, sugar beet, bananas, soya beans and rice; *Botrytis cinerea* (grey mould) on tomatoes, strawberries, vegetables, vines and other hosts and other *Botrytis spp.* on other hosts; *Alternaria spp.* on vegetables (e.g. cucumber), oil-seed rape, apples, tomatoes, cereals (e.g. wheat) and other hosts; *Venturia spp.* (including *Venturia inaequalis* (scab)) on apples, pears, stone fruit, tree nuts and other hosts; *Cladosporium spp.* on a range of hosts including cereals (e.g. wheat); *Monilinia spp.* on stone fruit, tree nuts and other hosts; *Didymella spp.* on tomatoes, turf, wheat and other hosts; *Phoma spp.* on oil-seed rape, turf, rice, potatoes, wheat and other hosts; *Aspergillus spp.* and *Aureobasidium spp.* on wheat, lumber and other hosts; *Ascochyta spp.* on peas, wheat, barley and other hosts; *Plasmopara viticola* on vines; other downy mildews such as *Bremia lactucae* on lettuce, *Peronospora spp.* on soybeans, tobacco, onions and other hosts, *Pseudoperonospora humuli* on hops and *Pseudoperonospora cubensis* on cucurbits; *Pythium spp.* (including *Pythium ultimum*) on turf and other hosts; *Phytophthora infestans* on potatoes and tomatoes and other *Phytophthora spp.* on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; *Sclerotinia spp.* on turf, peanuts, oil-seed rape and other hosts; *Sclerotium spp.* on turf, peanuts and other hosts; *Colletotrichum spp.* on a range of hosts including turf, coffee and vegetables; *Laetisaria fuciformis* on turf; *Mycosphaerella spp.* on banana, peanut, citrus, pecan, papaya and other hosts; *Diaporthe spp.* on citrus, soybean, melon, pear, lupin and other hosts; *Elsinoe spp.* on citrus, vines, olives, pecans, roses and other hosts; *Pyrenopeziza spp.* on oil-seed rape and other hosts; *Oncobasidium theobromae* on cocoa causing vascular streak dieback; *Fusarium spp., Typhula spp., Microdochium nivale, Ustilago spp., Urocystis spp., Tilletia spp.,* and *Claviceps purpurea* on a variety of hosts but particularly wheat, barley, turf and maize; *Ramularia spp.* on sugar beet and other hosts; post-harvest diseases particularly of fruit (e.g. *Pencillium digitatum* and *P. italicum* and *Trichoderma viride* on oranges. *Colletotrichum musae* on bananas and *Botrytis cinerea* on grapes); other pathogens on vines, notably *Eutypa lata, Guignardia bidwellii, Phellinus igniarus, Phomopsis viticola, Pseudopezicula tracheiphila* and *Stereum hirsutum;* other pathogens on lumber, notably *Cephaloascus fragrans, Ceratocystis spp., Ophiostoma piceae, Penicillium spp., Trichoderma pseudokoningii, Trichoderma viride, Trichoderma harzianum, Aspergillus niger, Leptographium lindbergi* and *Aureobasidium pullulans;* and fungal vectors of viral diseases e.g. *Polymyxa graminis* on cereals as the vector of barley yellow mosaic virus (BYMV).

Further, some of the compounds may be useful as seed dressings against pathogens including *Fusarium spp., Septoria spp., Tilletia spp.,* (e.g. bunt, a seed-borne disease of wheat), *Ustilago spp.* and *Helminthosporium spp.* on cereals, *Rhizoctonia solani* on cotton and *Pyricularia oryzae* on rice. In particular, some of the compounds show good eradicant activity against *Plasmopara viticola* and *Pythium ultimum*.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied to the foliage of plants, the compounds of the invention are applied at rates of 0.1 g to 10 kg, preferably 1 g to 8 kg, more preferably 10 g to 4 kg, of active ingredient (invention compound) per hectare.

When used as seed dressings, the compounds of the invention are used at rates of 0.0001 g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods, or applied by land or aerial irrigation systems.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invention are (RS)-1-aminopropyl-phosphonic acid, (RS)-4-(4-chlorophenyl)-2-phenyl-2-(1H-1,2,4-triazol-1-yl-methyl)

butyronitrile, (Z)-N-but-2-enyloxymethyl-2-chloro-2',6'-diethylacetanilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-g-butyrolactone, N-(2-methoxy-5-pyridyl)-cyclopropane carboxamide, alanycarb, aldimorph, ampropylfos, anilazine, azaconazole, BAS 490F, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, O,O-di-iso-propyl-S-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methyl-thioethylideneamino-oxycarbonyl)amino]thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, fluquinconazole, flusilazole, flutolanil, flutriafol, folpet, fuberidazole, furalaxyl, furametpyr, furconazole-cis, guazatine, hexaconazole, hydroxyisoxazole, hymexazole, ICIA5504, imazalil, imibenconazole, ipconazole, iprobenfos, iprodione, isopropanyl butyl carbamate, isoprothiolane, kasugamycin, mancozeb, maneb, mepanipyrim, mepronil, metalaxyl, metconazole, methfuroxam, metiram, metiram-zinc, metsulfovax, myclobutanil, NTN0301, neoasozin, nickel dimethyldithiocarbamate, nitrothal-isopropyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quintozene, rabenazole, sodium pentachlorophenate, streptomycin, sulphur, tebuconazole, techlofthalam, tecnazene, tetraconazole, thiabendazole, thicyofen, thifluzamide, 2-(thiocyanomethylthio)benzothiazole, thiophanate-methyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, triforine, triflumizole, triticonazole, validamycin A, vapam, vinclozolin, XRD-563, zineb and ziram. The compounds of general formula (I) can be mixed with soil, peat or other rooting media for the protection of plants against seed-borne, soil-borne or foliar fungal diseases.

The following Examples illustrate the invention. Throughout the Examples, the term 'ether' refers to diethyl ether, magnesium sulphate was used to dry solutions except where otherwise indicated, and solutions were concentrated under reduced pressure. All reactions were performed under an atmosphere of nitrogen and solvents were dried before use, where appropriate. Unless otherwise stated, chromatography was performed on a column of silica gel as the stationary phase. $^1$H NMR spectra were recorded using CDCl$_3$-solutions unless otherwise stated. NMR data are selective; no attempt is made to list every absorption in all cases. The following abbreviations are used throughout:

| NMR | = nuclear magnetic resonance | m | = multiplet |
|---|---|---|---|
| s | = singlet | br | = broad |
| d | = doublet | ppm | = parts per million |
| t | = triplet | mp | = melting point |
| q | = quartet | DMF | = N,N-dimethylformamide |
| | | THF | = tetrahydrofuran |

EXAMPLE 1

This Example illustrates the preparation of (E)-methyl 2-{2-[4-(2,2,2-trifluoroethoxy)pyrimidin-2-yloxy]phenyl}-3-methoxypropenoate (Compound of formula (I.1)).

To a solution of 4-chloro-2-methylthiopyrimidine (16.0 g) and potassium carbonate (27.6 g) in DMF (90 ml) at 0° C., was added with stirring a solution of 2,2,2-trifluoroethanol (10.0 g) in DMF (10 ml). Stirring was continued for 64 hours, then the reaction mixture was diluted with water and extracted with ether (3×150 ml). The combined extracts were washed with brine, dried and concentrated to give 2-methylthio-4-(2,2,2-trifluoroethoxy)pyrimidine (23.0 g, crude yield) as a clear pale orange oil, $^1$H NMR δ 2.57(3H, s); 4.79(2H,q); 6.54(1H,d); 8.33(1H,d) ppm.

To a solution of 2-methylthio-4-(2,2,2-trifluoroethoxy) pyrimidine (1.0 g) in glacial acetic acid (20 ml) at 15° C. was added a solution of potassium permanganate (2.4 g) in water (75 ml). When the addition was complete a solution of sodium metabisulphite (10% aqueous) was added until a clear solution was obtained. The reaction mixture was extracted with ether (3×70 ml), the combined extracts were washed with brine (3×), dried and concentrated to give 2-methanesulphonyl-4-(2,2,2-trifluorethoxy)-pyrimidine (1.0 g, 87% yield) as a clear oil; $^1$H NMR δ 3.35(3H,s); 4.91(2H,q); 7.11(1H,d); 8.69(1H,d) ppm.

To a solution of (E)-methyl 2-(2-hydroxyphenyl)-3-methoxypropenoate (0.81 g; prepared as described in Example 3 of EP-A-0242081) and potassium carbonate (0.54 g) in DMF (15 ml), was added dropwise a solution of 4-(2,2,2-trifluoroethoxy)-2-methanesulphonylpyrimidine (1.0 g) in DMF (10 ml). After stirring for 16 hours the reaction mixture was poured into water and extracted with ethyl acetate. The combined extracts were washed with brine, dried and concentrated to give an orange oil which was chromatographed using ether as the eluant, to give the title compound (0.294 g, 20% yield) as a clear oil; $^1$H NMR (270 MHz) δ 3.58(3H,s); 3.73(3H,s); 4.66(2H,q); 6.54(1H, d); 7.2–7.4(4H,m); 7.43(1H,s); 8.28(1H,d) ppm.

EXAMPLE 2

This Example illustrates the preparation of methyl 2-{2-[4-(2,2,2-trifluoroethoxy)pyrimidin-2-yloxy]phenyl}-glyoxalate-O-methyloxime (Compound of Formula (I.2)).

Dimethyl sulphate (5.7 g) was added dropwise to a suspension of 2,3-benzofurandione-3-oxime (5 g) and potassium carbonate (6.2 g) in THF (250 ml). After 16 hours the reaction mixture was concentrated and the residue diluted with water and extracted into ethyl acetate. The combined extracts were washed with brine, dried and concentrated to give a green oil, which was chromatographed using dichloromethane to give 2,3-benzofurandione-3-O-methyloxime (2.25 g, 41%) as a yellow solid m.p.76–78° C.; $^1$H NMR δ 4.34(3H,s); 7.15(1H,d); 7.22(1H,t); 7.50(1H,t); 7.99(1H,d) ppm.

Methanol (0.25 g) in DMF (3 ml) was added to a suspension of sodium hydride (0.192 g) in DMF (5 ml). After half an hour a solution of the 2,3-benzofurandione-3-O-methyloxime (1.35 g) in DMF (22 ml) was added. After stirring for 10 minutes a solution of 2-methanesulphonyl 4-(2,2,2-trifluoroethoxy)pyrimidine (1.98 g prepared as described in Example 1) in DMF (20 ml) was added. After 16 hours the reaction mixture was quenched with water and extracted into ethyl acetate. The combined extracts were washed with 2M sodium hydroxide solution, dried, concentrated and chromatographed using dichloromethane as the eluant to give the title compound (0.545 g, 19%) as a clear oil; $^1$H NMR δ 3.79(3H,s); 3.92(3H,s); 4.68(2H,q); 6.59(1H, d); 7.3–7.6(4H,m); 8.29(1H,d)ppm.

EXAMPLE 3

This Example illustrates the preparation of methyl 2-{2-[4-(2,2,2-trifluoroethoxy)pyrimidin-2-yloxy]phenyl}glyoxamide-O-methyloxime (Compound of formula (I.3)).

Methylamine (5 ml of a 33% ethanolic solution) was added to a suspension of 2,3-benzofurandione-3-O-methyloxime (1.27 g) in methanol (20 ml). After 2 hours the reaction was concentrated and the orange oil triturated with ether to give 2-hydroxyphenylglyoxamide-O-methyloxime (1.27 g, 85% yield) as a white solid; m.p.138°–9° C.; $^1$H NMR δ 2.98(3H,d); 4.01(3H,s); 6.9(1H,brs); 6.9–7.3(4H,m) ppm.

A mixture of 2-hydroxyphenylglyoxamide-O-methyloxime (1.26 g) and 2-methanesulphonyl-4-(2,2,2-trifluoroethoxy)pyrimidine (1.6 g) in DMF (40 ml) was added to a stirred suspension of potassium carbonate (1.7 g) in DMF (10 ml). After 3 hours the reaction was quenched with water and extracted into ethyl acetate. The combined extracts were washed with brine, dried, concentrated and chromatographed using ether as the eluant to give the title compound (1.81 g, 79% yield) as a clear oil; $^1$H NMR δ 2.83(3H,d); 3.81(3H,s); 4.68(2H,q); 6.56(1H,d); 7.2–7.5 (4H,m); 8.30(1H,d)ppm.

EXAMPLE 4

This Example illustrates the preparation of (E)-methyl 2-{2-[4-(1,1,1-trifluoroprop-2-oxy)pyrimidin-2-yloxy]phenyl}-3-methoxypropenoate (Compound of formula (I.4)).

A mixture of 2-methanesulphonyl-4-(1,1,1-trifluoroprop-2-oxy)-pyrimidine (3.07 g prepared using the method given in Example 1) and (E)-methyl 2-(2-hydroxyphenyl)-3-methoxypropenoate (2.5 g) in DMF (40 ml) was added to a suspension of sodium hydride (0.48 g) in DMF. After 2.5 hours the reaction was quenched with water and extracted with ethyl acetate. The combined extracts were washed with water, dried, concentrated and chromatographed using ether/hexane 3:1 as the eluant to give the title compound (1.1 g, 25% yield) as a pale yellow oil; $^1$H NMR δ 1.42(3H,d); 3.59(3H,s); 3.72(3H;s); 5.60(1H,m); 6.49(1H,d); 7.2–7.4 (4H,m); 7.44(1H,s); 8.20(1H,d)ppm.

EXAMPLE 5

Methyl 2-{2-[4-(1,1,1-trifluoroprop-2-oxy)pyrimidin-2-yloxy]phenyl}-glyoxalate-O-methyloxime (Compound of formula (I.5)).

This compound was prepared using the method given in Example 2 except that an equivalent amount of 2-methanesulphonyl-4-(1,1,1-trifluoroprop-2-oxy) pyrimidine was used in place of 2-methanesulphonyl-4-(2,2,2-trifluoroethoxy)pyrimidine. The compound was obtained as an oil; $^1$H NMR δ 1.44(3H,d); 3.79(3H,s); 3.91(3H,s); 5.62(1H,m); 6.53(1H,d); 7.3–7.6(4H,m); 8.26 (1H,d)ppm.

EXAMPLE 6

Methyl 2-{2-[4-(1,1,1-trifluoroprop-2-oxy)pyrimidin-2-yloxy]phenyl}-glyoxamide-O-methyloxime. (Compound of formula (I.6)).

This compound was prepared using the method given in Example 3 except that an equivalent amount of 2-methanesulphonyl-4-(1,1,1-trifluoroprop-2-oxy) pyrimidine was used in place of 2-methanesulphonyl-4-(2,2,2-trifluoroethoxy)pyrimidine. The compound was obtained as a solid; m.p. 87° C.; $^1$H NMR δ 1.42(3H,d); 2.83(3H,d); 3.79(3H,s); 5.64(1H,m); 6.51(1H,d); 6.64(1H, brs); 7.2–7.5(4H,brs); 8.27(d,s)ppm.

EXAMPLE 7

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. Tween 20 was added to give a final concentration of 0.05% when the sprays were applied to cereals.

For most of the tests the compounds were applied to the soil (roots) or to the foliage (by spraying) one or two days before the plant was inoculated with the disease. An exception was the test on *Erysiphe graminis* in which the plants were inoculated 24 hours before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

| | |
|---|---|
| 0 = 0% disease present | 20 = 10.1–20% disease present |
| 1 = 0.1–1% disease present | 30 = 20.1–30% disease present |
| 3 = 1.1–3% disease present | 60 = 30.1–60% disease present |
| 5 = 3.1–5% disease present | 90 = 60.1–100% disease present |
| 10 = 5.1–10% disease present | |

Each assessment was then expressed as a percentage of the level of disease present on the untreated control plants. This calculated value is referred to as a POCO (Percentage of Control) value. An example of a typical calculation is as follows:

Disease level on untreated control=90

Disease level on treated plant=30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values. The results are shown in Table 1.

TABLE 1

| Compound | Pr | Egt | Sn | Po | Tr | Vi | Pv | Pil |
|---|---|---|---|---|---|---|---|---|
| I.1 | 10 | 0 | 0 | 0 | 0 | 0 | 0 | 0 |
| I.4 | 0 | 0 | 0 | — | — | 0 | 0 | 0 |

—No result

Data represent activity following application as a combined foliar spray and root drench treatment at 100 ppm.

| Key to Diseases | | | |
|---|---|---|---|
| Pr | Puccinia recondita | Tc | Thanetophorus cucumeris |
| Egt | Erysiphe graminis tritici | Vi | Venturia inaequalis |
| Sn | Seotoria nodorum | Pv | Plasamopara viticola |
| Po | Pyricularia oryzae | Pi | Phytophthora infestans lycopersici |

CHEMICAL FORMULAE
(In Description)

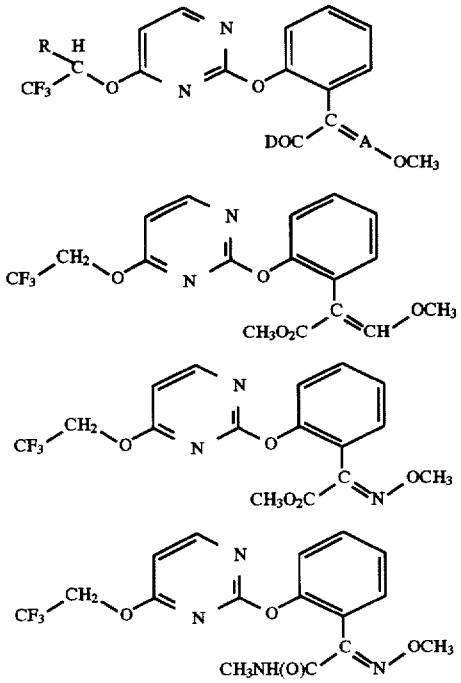

CHEMICAL FORMULAE
(In Description)

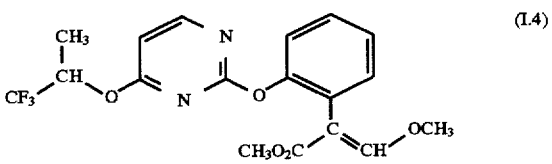
(I.4)

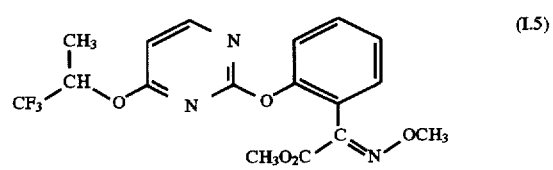
(I.5)

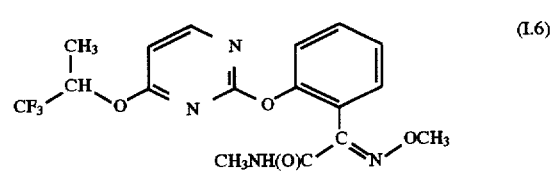
(I.6)

Scheme 1

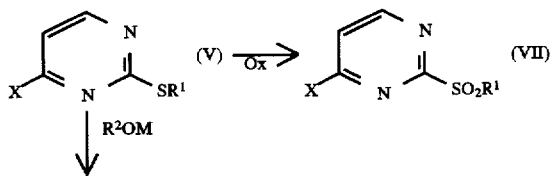

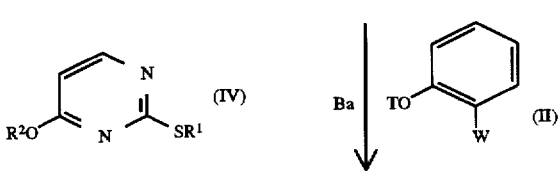

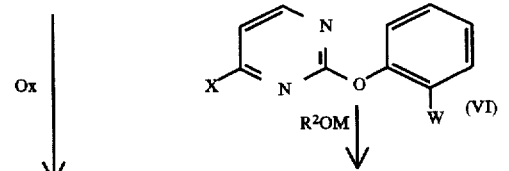

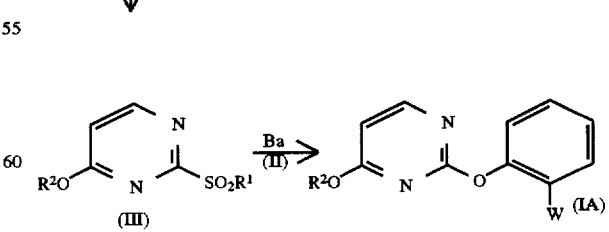

Scheme 2

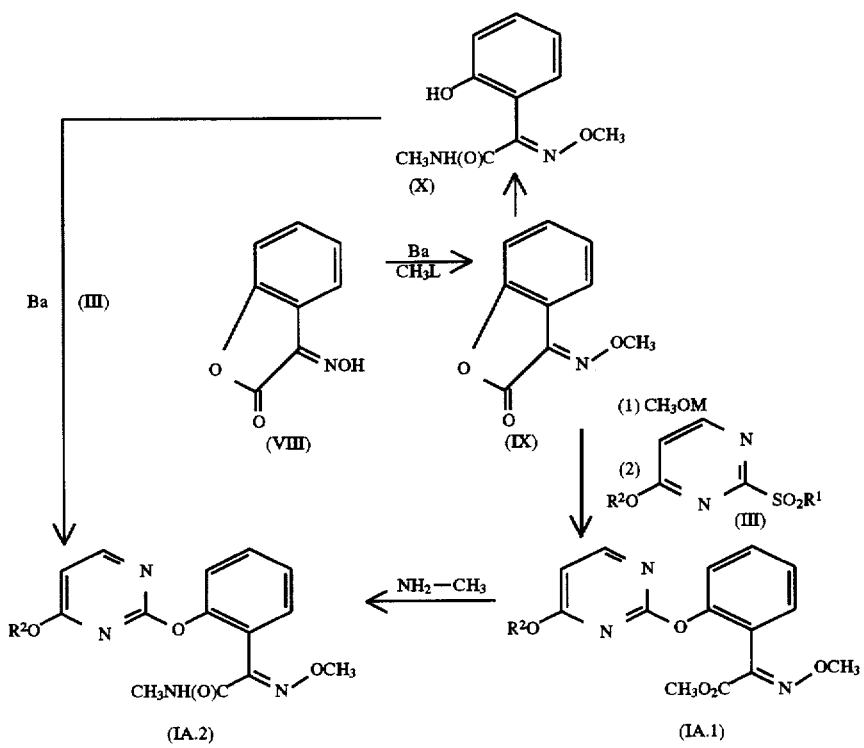

I claim:

1. A compound having the formula (I)

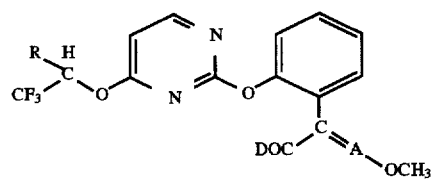

or a steroisomer thereof, wherein R is H or CH₃, A is CH or N, and D is OCH₃ or NHCH₃.

2. The compound (E)-methyl 2-{2-[4-(2,2,2-trifluoroethoxy)pyrimidin-2-yloxy]phenyl}-3-methoxypropenoate.

3. The compound (E)-methyl 2-{2-[4-(1,1,1-trifluoroprop-2-oxy)pyrimidin-2-yloxy]phenyl}-3-methoxypropenoate.

4. A compound selected from the group consisting of:

methyl 2-{2-[4-(2,2,2-trifluoroethoxy)pyrimidin-2-yloxy]phenyl}glyoxalate-O-methyloxime;

methyl 2-{2-[4-(2,2,2-trifluoroethoxy)pyrimidin-2-yloxy]phenyl}glyoxamide-O-methyloxime;

methyl 2-{2-[4-(1,1,1-trifluoroprop-2-oxy)pyrimidin-2-yloxy]phenyl}glyoxalate-O-methyloxime or methyl 2-{2-[4-(1,1,1-trifluoroprop-2-oxy)pyrimidin-2-yloxy]phenyl}glyoxamide-O-methyloxime.

5. A process for preparing a compound of formula I

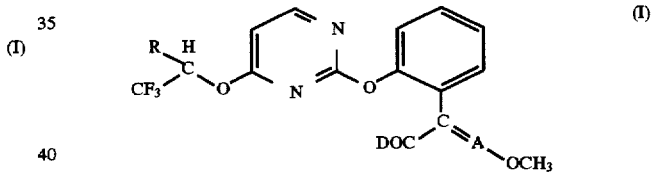

or a stereoisomer thereof, wherein R is H or CH₃, A is CH or N, and D is OCH₃ or NHCH₃ which comprises:

reacting a phenol of formula (II)

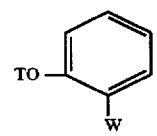

with a pyrimidinyl sulphone (III)

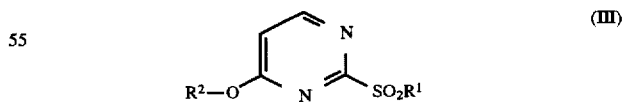

in the presence of a suitable base wherein $R^1$ is an alkyl or aryl group, $R^2$ is $CF_3CH_2$ or $CF_3CH(CH_3)$, T is hydrogen or an alkali metal, and W is the group DOC.C=A.OCH₃, wherein A and D have the meaning given in claim 1, or a group that can be transformed into group DOC.C=A.OCH₃.

6. A process according to claim 5 for preparing a compound of formula (IA.1) or (IA.2):

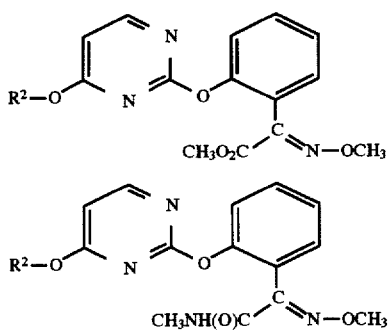

(IA.1)

(IA.2)

which further comprises the step of (a) treating a compound of formula (IX):

(IX)

with a compound of formula $CH_3OM$ and (b) treating the compound so formed with a pyrimidinyl sulphone of formula (III):

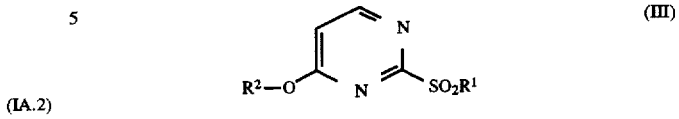

(III)

to form the compound of formula (IA.1) above; and, in order to obtain the compound of formula (IA.2), (c) treating the compound of formula (IA.1) with methylamine; wherein $R^1$ is an alkyl or aryl group, $R^2$ is $CF_3CH_2$ or $CF_3CH(CH_3)$ and M is an alkali metal.

7. A fungicidal composition comprising a fungicidally effective amount of a compound according to claim 1 and a fungicidally acceptable carrier or diluent therefor.

8. A method of combating fungi which comprises applying to plants, to the seeds of plants or to the locus of the plants or seeds, a compound according to claim 1.

9. A method of combating fungi which comprises applying to plants, to the seeds of plants or to the locus of the plants or seeds, a composition according to claim 7.

* * * * *